US010057510B2

(12) United States Patent
Stork et al.

(10) Patent No.: US 10,057,510 B2
(45) Date of Patent: Aug. 21, 2018

(54) SYSTEMS AND METHODS FOR ENHANCED INFRARED IMAGING

(71) Applicant: Rambus Inc., Sunnyvale, CA (US)

(72) Inventors: David G. Stork, Portola Valley, CA (US); Patrick R. Gill, Sunnyvale, CA (US)

(73) Assignee: Rambus Inc., Sunnyvale, CA (US)

( * ) Notice: Subject to any disclaimer, the term of this patent is extended or adjusted under 35 U.S.C. 154(b) by 239 days.

(21) Appl. No.: 14/930,144

(22) Filed: Nov. 2, 2015

(65) Prior Publication Data

US 2016/0073043 A1 Mar. 10, 2016

Related U.S. Application Data

(63) Continuation-in-part of application No. PCT/US2015/034966, filed on Jun. 9, 2015.

(60) Provisional application No. 62/015,369, filed on Jun. 20, 2014.

(51) Int. Cl.
*H04N 5/33* (2006.01)
*G02F 1/01* (2006.01)
*A61B 3/113* (2006.01)
*A61B 3/14* (2006.01)
*G02B 5/18* (2006.01)
*G02B 27/42* (2006.01)
*G06T 3/40* (2006.01)

(52) U.S. Cl.
CPC .............. *H04N 5/33* (2013.01); *A61B 3/113* (2013.01); *A61B 3/145* (2013.01); *G02B 5/1871* (2013.01); *G02B 27/4205* (2013.01); *G06T 3/4053* (2013.01)

(58) Field of Classification Search
CPC ..... H04N 5/33; G02B 27/4205; G02B 5/1871
See application file for complete search history.

(56) References Cited

U.S. PATENT DOCUMENTS

| 4,287,410 | A | 9/1981 | Crane et al. |
| 5,298,927 | A | 3/1994 | Konishi et al. |
| 5,536,924 | A | 7/1996 | Ackley |
| 5,703,637 | A | 12/1997 | Miyazaki et al. |

(Continued)

FOREIGN PATENT DOCUMENTS

| WO | WO-99/35523 | 7/1999 |
| WO | WO-2010-014084 A1 | 2/2010 |

OTHER PUBLICATIONS

Garcia-Martinez et al., "Generation of Bessel Beam Arrays Through Dammann Gratings", Mar. 20, 2012, vol. 51, No. 9, Applied Optics. pp. 1375-1381. 7 Pages.

(Continued)

*Primary Examiner* — Tsion B Owens
(74) *Attorney, Agent, or Firm* — Silicon Edge Law Group LLP; Arthur J. Behiel

(57) ABSTRACT

An infrared imaging system combines a low-resolution infrared camera with a high-resolution visible-light camera. Information extracted from images taken using the visible-light camera is combined with the low-resolution infrared images to produce an infrared image with enhanced spatial details. The process of extracting the information from the visible image adjusts the quantization level of the visible-light image to scale visible objects to match objects identified in the infrared image.

14 Claims, 8 Drawing Sheets

(56) References Cited

U.S. PATENT DOCUMENTS

| | | | |
|---|---|---|---|
| 5,870,503 | A | 2/1999 | Kumashiro |
| 6,121,616 | A | 9/2000 | Trigg |
| 6,122,062 | A | 9/2000 | Bieman et al. |
| 6,299,308 | B1 | 10/2001 | Voronka et al. |
| 6,344,893 | B1 | 2/2002 | Mendlovic et al. |
| 6,393,150 | B1 | 5/2002 | Lee et al. |
| 6,404,554 | B1 | 6/2002 | Lee et al. |
| 7,746,396 | B2 | 6/2010 | Mikkonen et al. |
| 7,924,312 | B2* | 4/2011 | Packard .............. H04N 5/2258 348/164 |
| 7,961,229 | B2 | 6/2011 | Soga |
| 8,153,972 | B2* | 4/2012 | DeMarco ................ G01C 3/08 250/330 |
| 8,368,741 | B2 | 2/2013 | Jelley et al. |
| 8,379,123 | B2 | 2/2013 | Townsend et al. |
| 8,565,547 | B2 | 10/2013 | Strandemar |
| 8,709,702 | B2 | 4/2014 | Flemming et al. |
| 9,055,248 | B2 | 6/2015 | Atif et al. |
| 9,369,612 | B2* | 6/2016 | Oh ....................... G06T 3/4038 |
| 2003/0103150 | A1 | 6/2003 | Catrysse et al. |
| 2007/0177819 | A1* | 8/2007 | Ma ..................... G06K 9/00771 382/284 |
| 2008/0170225 | A1 | 7/2008 | deBoer et al. |
| 2011/0109880 | A1 | 5/2011 | Nummela |
| 2011/0248151 | A1 | 10/2011 | Holcombe et al. |
| 2013/0050453 | A1 | 2/2013 | Bergstrom et al. |
| 2013/0077049 | A1 | 3/2013 | Bohn |
| 2013/0321641 | A1* | 12/2013 | McManus ............ H04N 5/2254 348/164 |
| 2014/0071400 | A1 | 3/2014 | Gao |
| 2015/0187828 | A1 | 7/2015 | Salsman |

OTHER PUBLICATIONS

Guerineau et al., "Generation of Achromatic and Propagation-Invariant Spot Arrays by Use of Continuously Self-Imaging Gratings," Apr. 1, 2001, vol. 26, No. 7, Optics Letters. pp. 411-413. 3 Pages.

Barth, Phillip et al., "Thin Linear Thermometer Arrays for Use in Localized Cancer Hypertermia", IEEE Transactions on Electron Devices, vol. ED-29, No. 1, Jan. 1982, pp. 144-150. 7 Pages.

Bautu, Andrei et al., "Tikhonov Regularization in Image Reconstruction with Kaczmarz Extended Algorithm", 18th Symposium Simulationstechnique ASIM 2005 Proceedings, 2005. 6 Pages.

De Wilde, Yannick, "Thermal Radiation Scanning Tunnelling Microscope (TRSTM): Near-Field Imaging and Spectroscopy Probe of teh Thermal Emission", ESPCI Paris Tech, Nanoscale Radiative Heat Transfer, May 13, 2013. 47 Pages.

Gill, Patrick et al., "Lensless Ultra-Miniature Imagers Using Odd-Symmetry Spiral Phase Gratings", article presented at Computational Optical Sensing and Imaging (COSI), Arlington, Virginia, Jun. 23-27, 2013. 3 pages.

Gill, Patrick et al., "Lensless Ultra-Miniature Imagers Using Odd-Symmetry Spiral Phase Gratings", slide deck presented at Computational Optical Sensing and Imaging (COSI), Arlington, Virginia, Jun. 23-27, 2013. 18 pages.

Gill, Patrick et al., "The In-Crowd Algorithm for Fast Basis Pursuit Denoising", IEEE Transactions on Signal Processing, vol. 59, No. 10, Oct. 2011, pp. 4595-4605. 11 Pages.

Glolab Corporation, "How Infrared Motion Detector Components Work", www.glolab.com/pirparts/infrared.html, Jun. 17, 2014. 3 Pages.

Hamamatsu Photonics K.K., Solid State Division, "Technical Information SD-12 Characteristics and Use of Infrared Detectors", Mar. 2011, pp. 1-42. 43 pages.

Hashemi, Sayed Masoud et al., "Efficient Low Dose X-Ray CT Reconstruction Through Sparsity-Based Map Modeling", arXiv:1402.1801V1 [stat.AP], Feb. 8, 2014, pp. 1-10. 10 Pages.

ISR—Notification of Transmittal of the International Search Report and the Written Opinion of the International Searching Authority dated Oct. 16, 2015 re Intl. Appln. No. PCT/US2015/034966. 11 Pages.

Kittel, A. et al., "Near-Field Thermal imaging of Nanostructured Surfaces", Applied Physics Letters 93, Nov. 12, 2008. 3 Pages.

Liu, ZE et al., "An Image Reconstruction Algorithm Based on Tikhonov Regularization in Electromagnetic Tomography", 2010 International Conference on Measuring Technology and Mechatronics Automation, pp. 488-491, 4 Pages.

Morrison, Rick L., "Symmetries that simplify the design of spot array phase gratings", Journal of the Optical Society of America A, vol. 9, Issue 3, pp. 464-471, 1992. 8 pages.

Nakashima, Shota et al., "Image Reconstruction Method for Human Shape Detection Using One-Dimensional Brightness Distribution Sensor", The Proceedings of the 1st International Conference on Industrial Application Engineering 2013 Japan, 2013, pp. 244-248, 5 Pages.

Sauvola, J., et al., "Adaptive Document Image Biniarization", The Journal of the Pattern Recognition Society, vol. 33, 1999, pp. 225-236. 12 Pages.

Stork, David et al, "Lensless Ultra-Minature CMOS Computational Imagers and Sensors" SensorComm 2013, Barcelona, Spain, Aug. 26, 2013. 59 Pages.

Wikipedia, "Microbolometer", Downloaded from http://en.wikipedia.org/w/index.php?oldid=603593009, 2015. 6 Pages.

Wikipedia, "Thermographic Camera", Downloaded from http://en.wikipedia.org/w/index.php?oldid=60960328, 2015. 8 Pages.

* cited by examiner

SYSTEMS AND METHODS FOR ENHANCED INFRARED IMAGING

BACKGROUND

The materials used in the manufacture of IR lenses (e.g., monocrystalline Germanium) are generally expensive relative to materials used in the manufacture of lens for visible or near-visible light, and the cost of IR lenses tends to scale with the cube of their linear size. As a result, IR sensors are made small to reduce the cost to a practical level. Thus one needs small, highly accurate thermal sensors. There are only a few materials and techniques able to give good room-temperature thermal performance in a pixel of the scale of thermal wavelength (about 10 µm) on a side. High-quality vacuum-sealed thermal transducers are the current industry standard because they offer adequate performance at the appropriate size. However, such transducers are prohibitively expensive for many applications.

IR image sensors sensitive to wavelengths in a range such as 3 to 30 microns generally produce images that are of low resolution relative to those that sense visible or near-visible light in a range such as 300 to 1200 nm. In this context, high and low-resolution refer to information content, not necessarily the number of pixels in an image. A very blurry infrared energy image sampled by a microbolometer or thermopile sensor array comprising a large number of pixels may nevertheless be considered "low-resolution" because of the optics and thermal properties of the scene and the response functions of the sensing pixels. Whatever the pixel count, infrared images may be ineffective for providing viewers with sufficient information, such as image details for tasks such as accurately counting objects, animals, or people.

BRIEF DESCRIPTION OF THE DRAWINGS

The detailed description is illustrated by way of example, and not by way of limitation, in the figures of the accompanying drawings and in which like reference numerals refer to similar elements and in which.

DETAILED DESCRIPTION

Figure 1A:
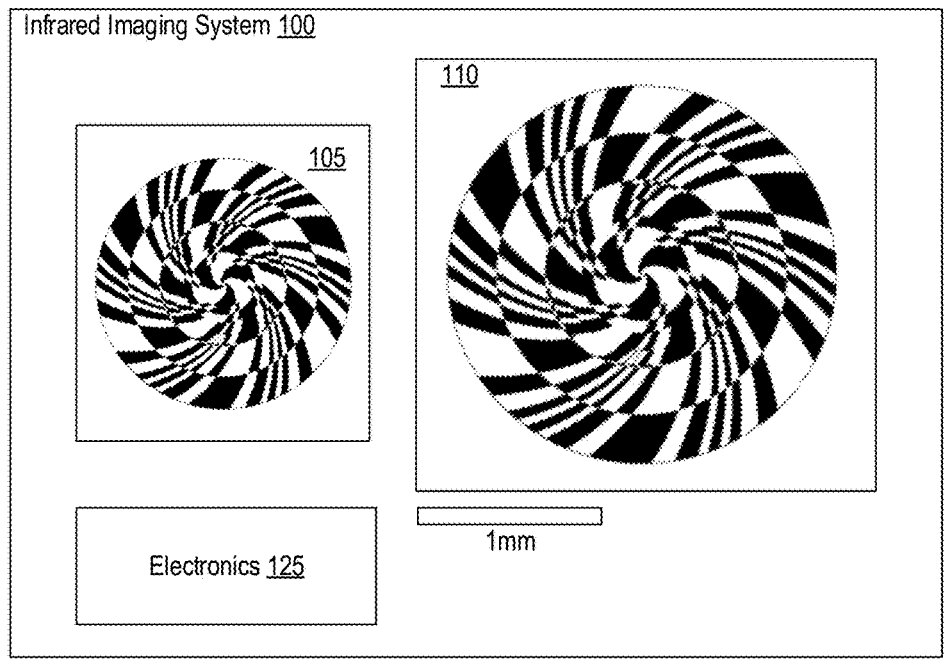
FIG. 1A is a plan view of a hybrid imaging system 100 that combines a visible-light camera 105 with an infrared camera 110.
Figure 1B:
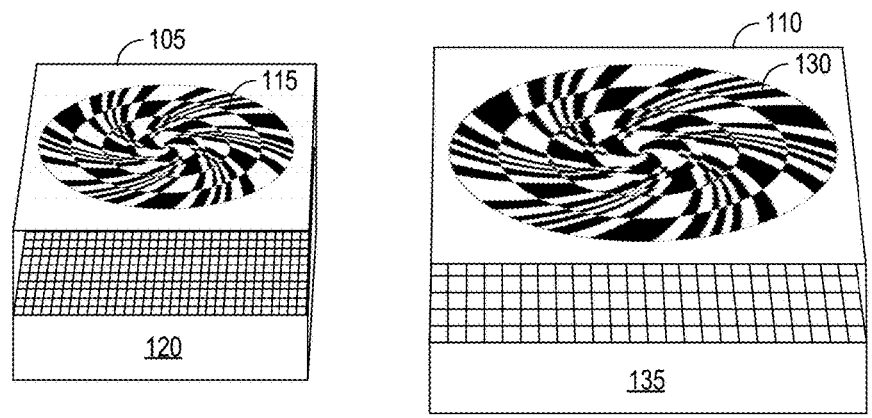
FIG. 1B shows cameras 105 and 110 of FIG. 1A from the side.

FIG. 1A is a plan view of a hybrid imaging system 100 that combines a visible-light camera 105 with an infrared (IR) camera 110. FIG. 1B shows cameras 105 and 110 from the side. Images from IR camera 110 are enhanced to render them more suitable for human observers by adding information from relatively high-resolution visible-light images of the same scene taken by camera 105.

Visible-light camera 105 includes an optical element 115—a phase grating in this example—overlying a photo-detector array 120, such as a CCD (charge-coupled device) or CMOS (complementary metal-oxide-semiconductor) sensor. Element 115 focuses incident visible light to form an interference pattern on array 120. The interference pattern is unintelligible to a human observer, but includes sufficient information to allow the image or aspects of the image to be computed. In this example, array 120 captures the interference pattern and electronics 125 integrated with or separate from system 100 computes a visible-light image from the pattern.

Infrared camera 110 includes an optical element 130 overlying an infrared detector 135, such as a microbolometer or thermopile sensor array. Element 130 focuses incident infrared light to form an interference pattern on detector 135. Detector 135 captures the resultant infrared interference pattern and electronics 125 computes an infrared image from the pattern. The effective resolution of this infrared image can be low relative to the image acquired by visible-light camera 105. As detailed below, information extracted from the visible-light image taken by camera 105 is combined with the infrared image from camera 110 to produce an infrared image with enhanced spatial details.

Black and white areas within each of optical elements 115 and 130 represent relatively high and low features that define periodic boundaries of substantially odd symmetry. These features induce near-field diffraction and concomitant near-field spatial modulations that produce interference patterns for capture by the underlying arrays 120 and 135. Images and other image data can be extracted from these captured patterns. For a detailed discussion of optical systems that employ phase gratings to image visible and infrared light, see international application PCT/US2015/034966 to Patrick R. Gill and David G. Stork (10203WO01), published 23 Dec. 2015 as International Publication WO2015/195417 A1, entitled "Systems and Methods for Lensed and Lensless Optical Sensing", which is incorporated herein by reference. Either or both cameras 105 and 110 can employ refractive optics in other embodiments. In one embodiment, for example, the visible camera is a traditional lens-based system that captures relatively high-resolution color or black-and-white images, whereas camera 110 employs diffractive optics of the type detailed in Gill and Stork, supra. The materials used in the manufacture of IR lenses (e.g., monocrystalline Germanium) are generally expensive relative to that for visible light, and the cost of IR lenses tends to scale with the cube of their linear size. In some embodiments, camera 110 does not require a separate lens, and thus can dramatically reduce the size and volume of expensive infrared transmissive material. Moreover, a thin diffraction grating can be composed of a low-cost material (such as polyethylene) whose transparency is satisfactory in a 50 micron-thick diffraction grating even though a thick lens made from the material would be nearly totally opaque in thermal IR bands.

Figure 1C:
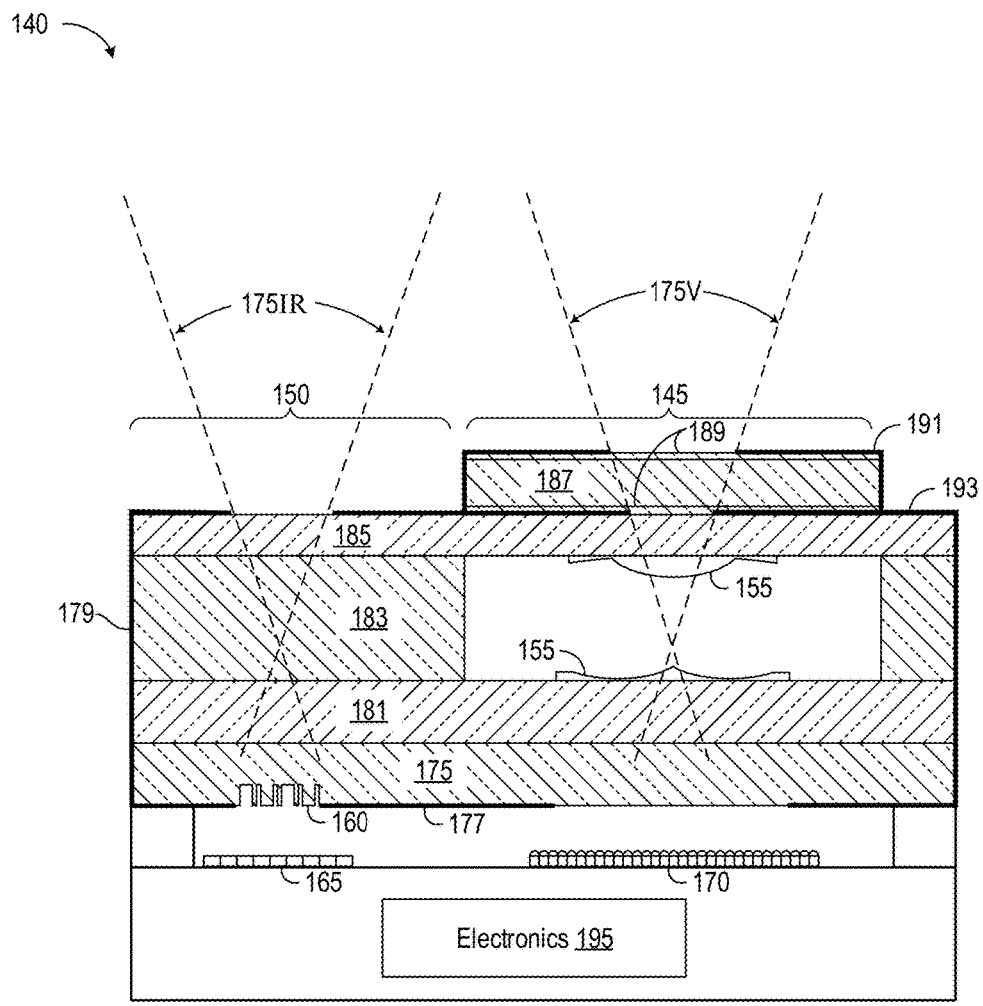
FIG. 1C is a cross-sectional view of a hybrid imaging system 140 that combines a lens-based camera 145 with a grating-based IR camera 150.

FIG. 1C is a cross-sectional view of a hybrid imaging system 140 that combines a lens-based camera 145 with a grating-based IR camera 150 of the type detailed previously in connection with FIGS. 1A and 1B. In capturing images, refractive optics 155 and a phase grating 160 produce respective responses on underlying and respective IR and visible-light sensitive arrays 165 and 170. The refractive and diffractive responses have different attributes that system 140 uses to enhance overall imaging performance. In this embodiment, refractive optics 155 capture high-resolution color images over a field of view 175V and phase grating 160 captures low-resolution IR images over approximately the same field of view 175IR. These fields are offset from one another, so the IR and visible-light images are registered in subsequent processing.

IR array 165 can be e.g. a thermopile array, and visible-light array 170 e.g. a CMOS or CCD photodetector array with or without microlenses. Grating 160 is cast or etched into an area of the bottom of a glass carrier wafer to form a phase-grating layer 175. An opaque aperture layer 177 of e.g. metal limits cross coupling of responses from the different diffractive and refractive optics. An opaque coating 179 prevents light from entering via the sides.

Camera 145 is formed using a stack of glass layers 181, 183, 185, 187, and 189. From the top, glass layer 187 is disposed between a pair of infrared (IR) filters 189, and a pair of opaque layers 191 and 193 in which are formed apertures for cameras 145 and 150. An opening in glass layer 183 contains refractive optics 155—a pair of opposing lenses—that cast a focused refractive response onto photodetector array 170. System 140 can include e.g. a pinhole and/or focusing optics in other embodiments.

Phase grating 160 is framed by an aperture in layer 177. A second aperture in layer 193 limits the field of view, in part to block light reflected of the sides of the portion of camera 145 that protrudes from system 140. Incident light traverses the glass layers to impinge on grating 160, which casts a diffractive response—an interference pattern—onto array 165. Some integrated or separate electronics 195 processes data captured by arrays 165 and 170 to create a hybrid image with both IR and visible-light data.

Figure 2:
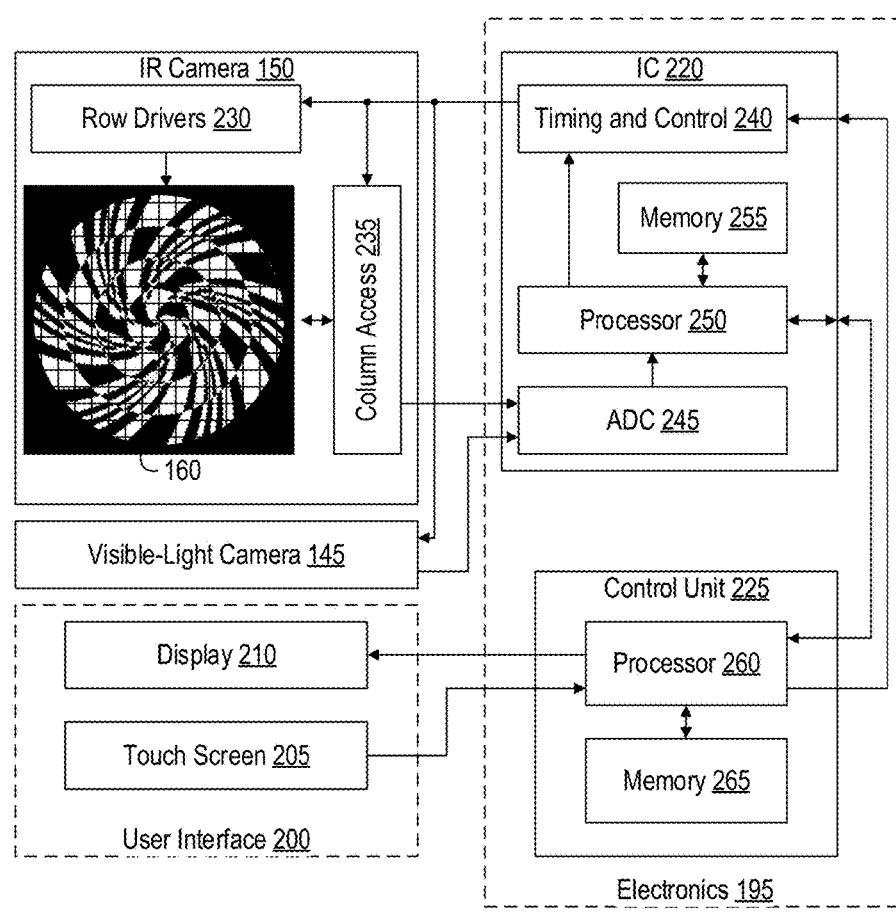
FIG. 2 schematically depicts imaging system 100 of FIG. 1A.

FIG. 2 schematically depicts imaging system 140 of FIG. 1C. As noted previously, computer 140 includes IR and visible-light cameras 150 and 145, and some integrated or separate electronics 195. System 100 additionally includes a user interface 200 with an input mechanism 205 (e.g., a touchscreen) and a display 210. Electronics 195 includes a monolithic integrated-circuit device (IC) 220 for controlling and extracting image data from cameras 145 and 150, and a central control unit 225 for managing touchscreen user interface 200 and IC 515. IC 220 can be separate from or integrated with one of the cameras, or the functionality provided by IC 220 can be divided between them in other embodiments. Some or all of the functionality provided by control unit 225 can likewise be integrated with, separate from, or distributed among other components.

IR camera 150 includes optical element 160 over array 165, pixels of which are visible below features of element 160. Row drivers 230 and column-access circuitry 235 provide access to the rows and columns of pixels. IC 220 includes timing and control circuitry 240, which controls row drivers 230 and column access circuitry 235 to direct the pixels to convey analog image data to an analog-to-digital converter (ADC) 245. A processor 250 with access to integrated memory 255 processes the digital data from ADC 245 to produce image data for conveyance to control unit 225. The image data can represent the raw intensities captured by imaging devices 105 and 110, or processor 250 can process the image data to provide more information about the imaged scene. For example, processor 250 might estimate the received light fields for camera 150 to produce human-recognizable images from the captured IR interference patterns. Control unit 225 includes a processor 260 and memory 265 to control and interact with user interface 200. Responsive to input from touchscreen 205, processor 260 directs IC 220 to produce a combined image using image data from both cameras 145 and 150. Processor 250 may include a dedicated graphical processor or controller to control and manipulate the content provided to the user on display 120. IC 220 and control unit 225 can be standalone ICs or part of a system on a chip (SoC) that may support diverse imaging functions.

Figure 3:
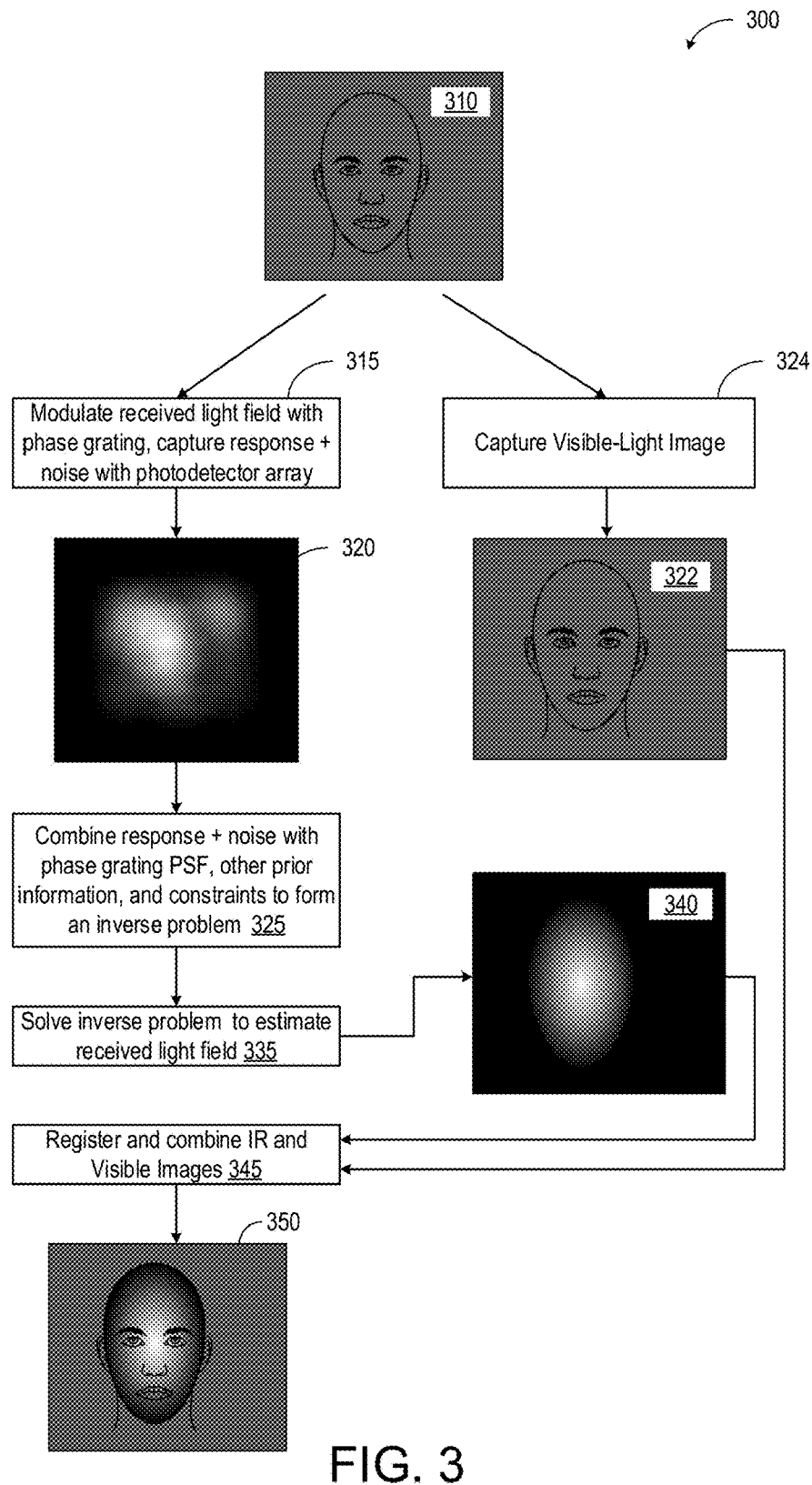
FIG. 3 is a flowchart 300 detailing how an image 305 is captured and resolved by camera 105 (camera 110 works similarly).

FIG. 3 is a flowchart 300 detailing how an image is captured and resolved by hybrid imaging system 140 of FIG. 1C. First, system 140 is directed at a scene 310 that includes both IR and visible-light attributes. The incident light passes through phase grating 160 to produce an intensity pattern 320 on an underlying two-dimensional array 160, which captures the pattern (315). The captured pattern 320 may appear unintelligible to a human; however, because grating 160 has sharp features in its point-spread function (PSF), the pattern contains rich information about the image. Visible-light camera 145 simultaneously captures a visible-light image 322 (324). Visible-light image 322 may have poor contrast due to low light, but includes some spatial information not found in pattern 320.

The PSF of grating 160, possibly in combination with the underlying array, is known from a prior calibration or high-fidelity simulation. The way in which the PSF varies as a function of incident angle and color may also be similarly determined. A mathematical conversion based on this response can thus be used to construct an image of the IR aspects of scene 310 from pattern 320. Responses 320 and 330 are combined to form an inverse problem (325), which is solved (335) to recover an IR version 340 of scene 310. One embodiment employs the well-known Tikhonov regularized inversion technique to accomplish steps 325 and 335. In this example, a human face that is warm relative to the background appears as a bright region against a dark background.

Next, in step 345, the visible-light and IR images 322 are registered and combined to form a composite image 350. Registration matches the fields of view provided by the IR and visible-light images 340 and 322, and uses spatial information from image 322 to constrain the relatively low-resolution IR image 340 to yield the higher-resolution thermal image 350.

Figure 4A:
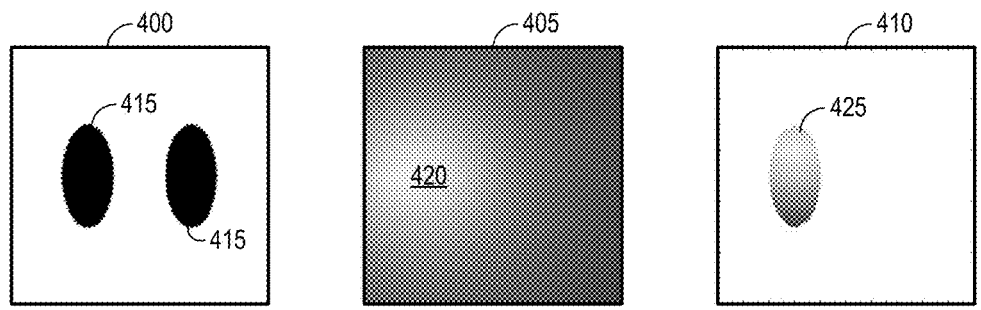
FIG. 4A illustrates how a high-resolution visible-light image 400 can be used to constrain a relatively low-resolution infrared image 405 to yield a higher-resolution infrared image 410.

FIG. 4A illustrates how a high-resolution visible-light image 400 can be used to constrain a relatively low-resolution infrared image 405 to yield a higher-resolution infrared image 410. Image 400 includes two objects 415 that might represent human figures. The infrared image 405 includes a bright area 420 indicative of warmth, but is of low effective resolution. Thus the number and location(s) of the source(s) is difficult to discern. Combining images 400 and 410 provides infrared image 415 (where the pixel values correspond to infrared intensity or thermal temperature) with sharp spatial constraints. That is, image 415 has effectively higher spatial resolution than infrared image 405. In this schematic example, image 415 resolves the ambiguities of images 400 and 405; the image depicts one warm body 425 at the left location indicated in image 400.

Figure 4B:
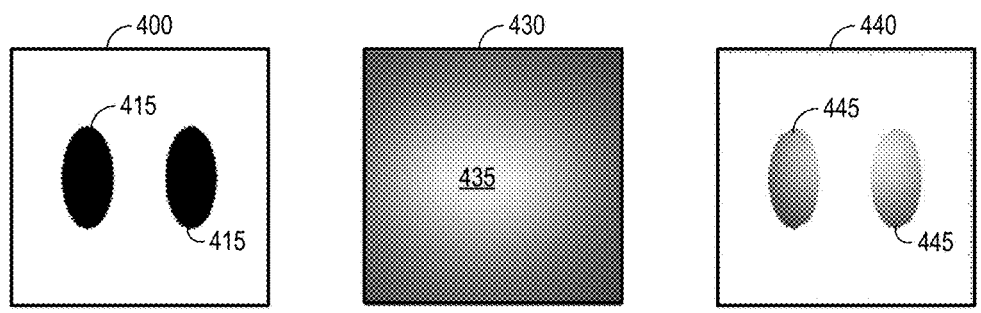
FIG. 4B is an illustration similar to FIG. 4A, with an identical visible-light image 400.

FIG. 4B is an illustration similar to FIG. 4A, with an identical visible-light image 400. However, the corresponding infrared image 430 shows a relatively broad bright area 435 that, due to the low effective resolution, is indicative of an ambiguous number of warm bodies. Combining images 400 and 430 provides infrared image 440 with sharp spatial constraints that resolve the ambiguities of images 400 and 405; the image depicts two warm bodies 445.

Figure 5A:
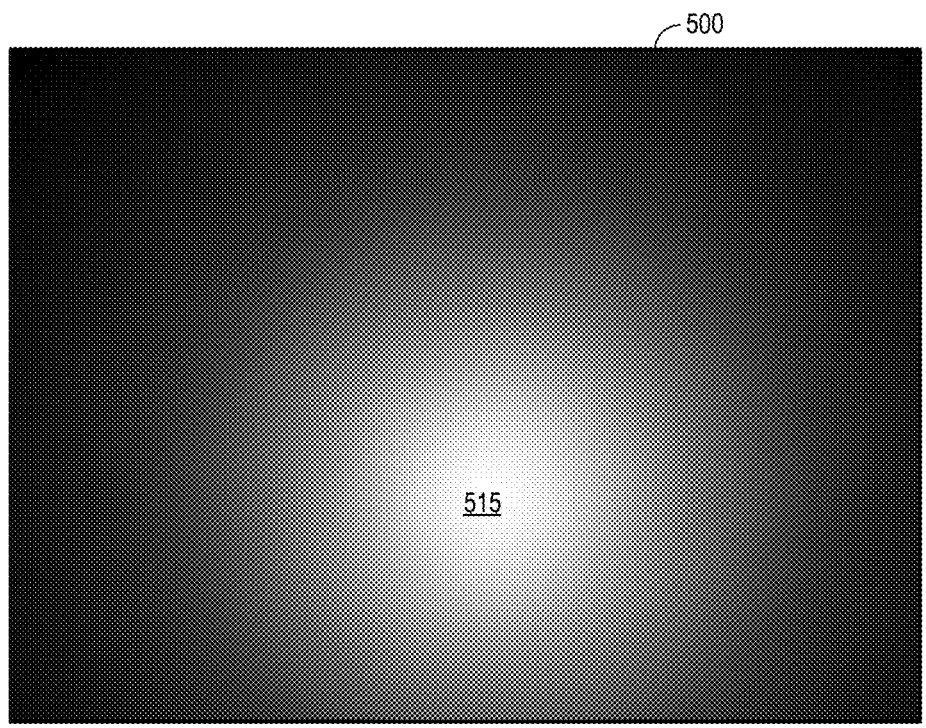
FIGS. 5A and 5B respectively depict an infrared image 500 and a visible-light image 505 of the same scene.
Figure 5B:
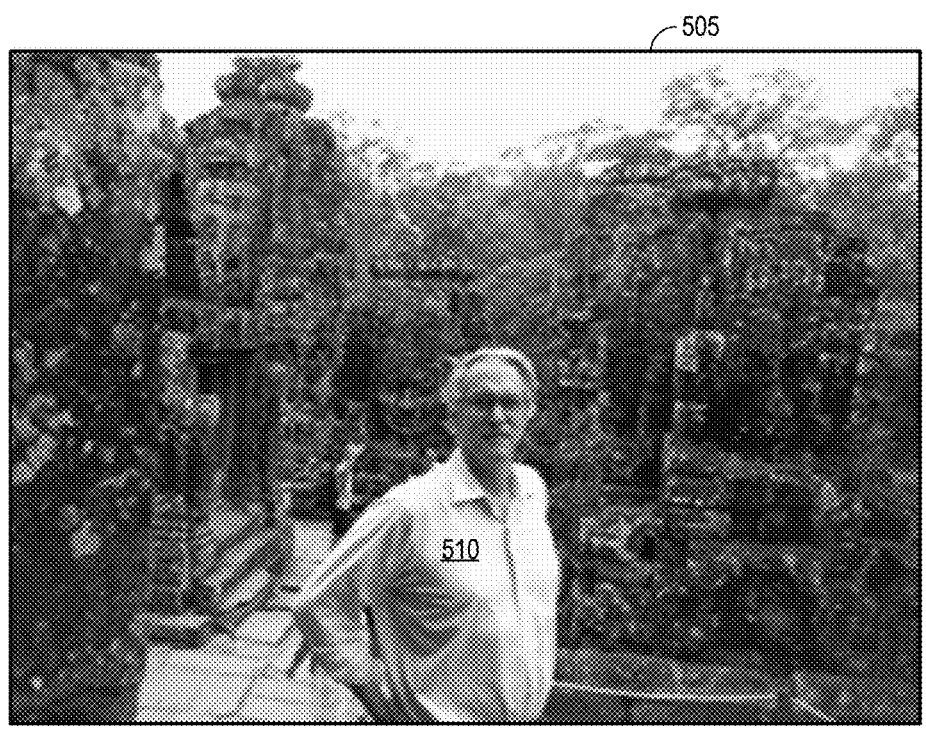

FIGS. 5A and 5B respectively depict an infrared image 500 and a visible-light image 505 of the same scene, and are used in the following example to illustrate a method of adding spatial information to infrared images. The scene includes a human subject 510 that is warm relative to the background, and is thus depicted in infrared image 500 as an area 515 of relatively high intensity. In the embodiment of FIG. 2, IC 200 provides control unit 225 with both images 500 and 505 responsive to user input. Cameras 105 and 110 are calibrated and registered with one another so that images 500 and 505 represent coextensive areas of the scene.

Figure 6A:
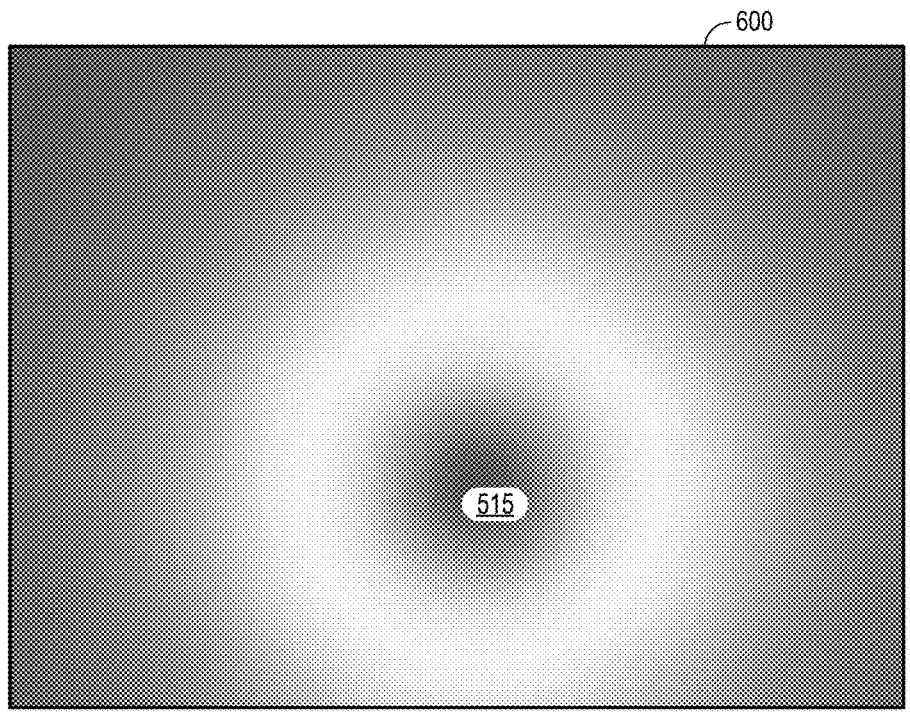
FIG. 6A is a pseudo-color thermal infrared image 600 of the scene in FIG. 5B, containing the same information as in FIG. 5A (the pseudo-color image is rendered in greyscale).

FIG. 6A is a pseudo-color thermal infrared image 600 of the scene in FIG. 5B, containing the same information as in FIG. 5A (the pseudo-color image is rendered in greyscale). In this embodiment image 500 is represented using fewer pixels than image 505, so image 500 is upsampled such that image 600 has the same numbers of rows and columns of pixels as image 505. This depiction clarifies the scale of the illuminating subject, providing measures of area and location of the area 515 that corresponds to subject 510. Processor 260 (FIG. 2) processes image 600 or the like to identify the thermal image object 515 within the imaged scene, and to determine its area and position.

Figure 6B:
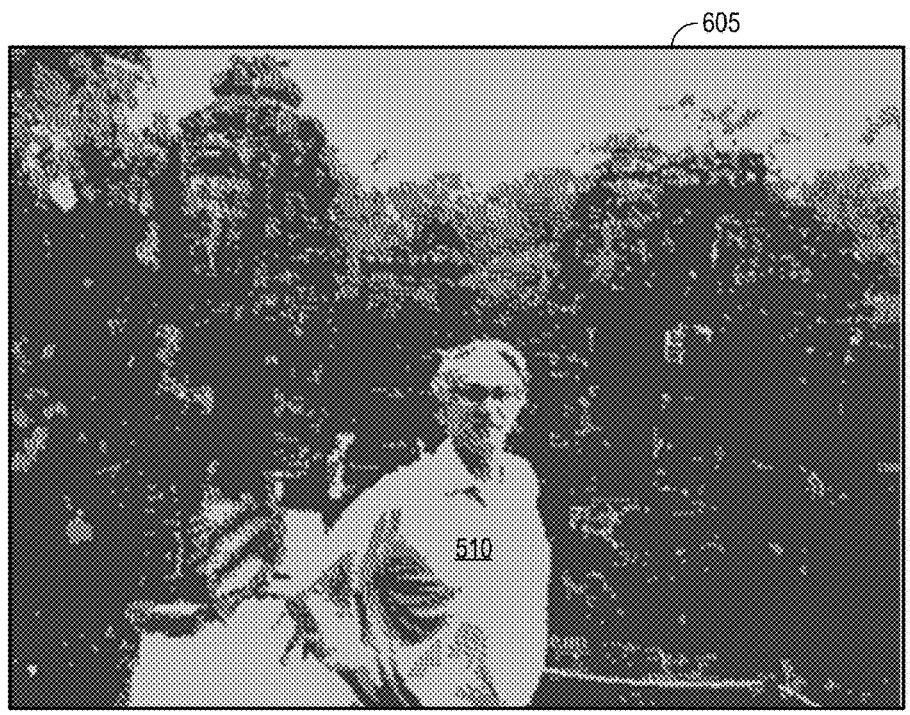
FIG. 6B depicts a chromaticity-based quantized version 605 of the high-resolution visible image 505 of FIG. 5B.

FIG. 6B depicts a chromaticity-based quantized version 605 of the high-resolution visible image 505 of FIG. 5B. Regions that are similar in color (and hence likely from the same object) are assigned similar pixel values. Visible image 505 is quantized to include a number n of pixel classes. Processor 260 alters the quantization level of image 605— the number of pixel classes—until the area of object 515 within image 600 contains a feature of similar scope in image 605. Processor 260 can do this iteratively to find the quantization level that provides the best fit. In this example, the selected quantization level renders most of subject 510 in the same shade (the same pixel value), and the area occupied by that shade approximates the area and location of area 515 of FIG. 6A. Image resolution, or other image variables, can also be altered to match the area of object 515 with features of the visible image. Having determined a suitable quantization level for the visible-light image, processor 260 adds the information from the thermal-object area 515 to the scaled visible-object area to produce a combined image.

Figure 7A:
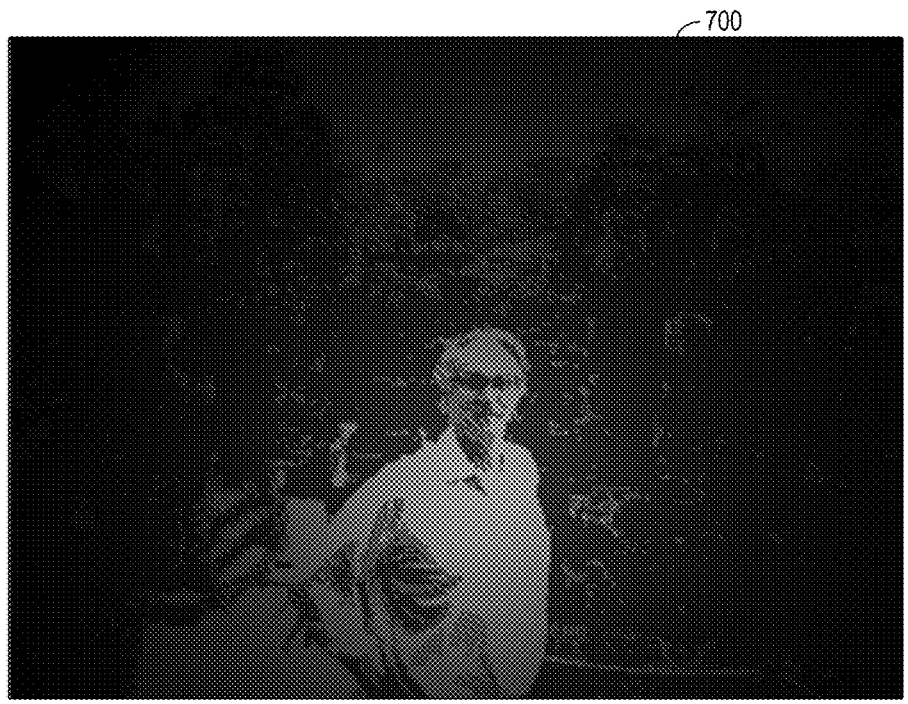
FIG. 7A is an example of a combined image 700 computed based on the low-resolution infrared image 500 (FIG. 5A) and the higher-resolution visible image 505 (FIG. 5B) using nonlinear pixel-based image computation.

FIG. 7A is an example of a combined image 700 computed based on the low-resolution infrared image 500 (FIG. 5A) and the higher-resolution visible image 505 (FIG. 5B) using nonlinear pixel-based image computation. Even though the sky and the shirt had similar visible chromaticities, the sky does not appear here because there was no infrared signature or signal from the sky region.

Figure 7B:
FIG. 7B is pseudo-color rendering 705 of the enhanced resolution computed infrared image of FIG. 7A, shown here in greyscale.

FIG. 7B is pseudo-color rendering 705 of the enhanced resolution computed infrared image of FIG. 7A, shown here in greyscale. Relatively warm and cool areas are depicted on a scale from red to blue.

Other embodiments employ an image-processing method called "region binarization," in which a chromatically segmented region of the high-resolution visible image is selected by some feature of the low-resolution infrared image (such as the location of its peak intensity or highest temperature source). The high-resolution visible segment can then be "painted" or "filled" with the area-average value of the low-resolution infrared image. In this way, the infrared information fills a high spatial resolution region describing the scene. Another aspect of enhancing the resolution of a low-resolution image is performing nonlinear image arithmetic using high- and low-resolution images. First, the low-resolution (infrared) image is over-sampled to match that of the high-resolution image. (This step is not used if the two images have the same number of pixels.) Second, the pixel-by-pixel mathematics, for instance thresholding or segmenting the visible image and multiplying each of its pixel values by the corresponding pixel values in the low-resolution image, then thresholding the result. Because the pixel scale is high, the final image can have the spatial resolution (spatial information) of the high-resolution visible image.

While the subject matter has been described in connection with specific embodiments, other embodiments are also envisioned. For example, the wavelength band of interest can be broader or narrower than those of the foregoing examples, and may be discontinuous; and cameras and gratings detailed herein can be adapted for use in multi-aperture or programmable-aperture applications. Other variations will be evident to those of skill in the art. Therefore, the spirit and scope of the appended claims should not be limited to the foregoing description. Only those claims specifically reciting "means for" or "step for" should be construed in the manner required under the sixth paragraph of 35 U.S.C. § 112.

What is claimed is:

1. An optical system comprising:
   a photodetector array to detect first light of a wavelength within a wavelength band from 300 nm to 1200 nm of a scene, the photodetector array representing the detected first light as first image information;
   an optical element overlying the photodetector array to focus the first light on the photodetector array;
   an infrared imaging device for detecting infrared light including some wavelength within an infrared wavelength band from 3 microns to 30 microns of the scene, the infrared imaging device representing the detected infrared light as second image information;
   a phase grating illuminating a pattern on the infrared imaging device responsive to the infrared light; and
   at least one processor to combine the first image information representing the first light of the scene detected by the photodetector array with the second image information derived from the infrared light of the scene detected by the infrared imaging device.

2. The optical system of claim 1, wherein combining aspects of the first light of the scene with the information derived from the infrared light of the scene includes identifying a first object and a corresponding infrared object in the respective first and infrared images.

3. The optical system of claim 2, further comprising adjusting a quantization level of the detected first light to scale the first object to the infrared object.

4. The optical system of claim 1, wherein the at east one processor sorts pixels of the detected first light by color.

5. The optical system of claim 1, wherein the at east one processor upsamples a resolution of the infrared image to match a resolution of the detected first light.

6. The optical system of claim 1, wherein the optical element is a diffractive optical element.

7. A method comprising:
capturing infrared light within a wavelength band from 3 microns to 30 microns to produce an infrared image of a scene;
processing the infrared image to identify a thermal image object within the scene, the thermal image object occupying a thermal object area of the infrared image;
capturing second light within a wavelength band from 300 nm to 1200 nm to produce a second image of the scene;
processing the second image to identify a second image object occupying a second-object area overlapping the thermal object area;
adjusting a quantization level of the second image to scale the second-object area to the thermal-object area to produce a scaled image; and
combining information from the thermal-object area with information from the scaled image to produce a combined image.

8. The method of claim 7, adjusting the quantization level comprises sorting pixels of the second image by color.

9. The method of claim 7, wherein capturing the infrared light comprises:
modulating incident light to induce near-field spatial modulations that illuminate a pattern;
capturing the pattern to produce a set of intensity values for the captured pattern; and
extracting an estimate of the scene from the intensity values.

10. The method of claim 9, wherein the estimate of the scene includes fewer pixels than the second image, the method further comprising upsampling the estimate of the scene.

11. The method of claim 7, wherein the infrared image is of a first resolution, the second image is of a second resolution higher than the first resolution, and the combined image is of a third resolution between the first resolution and the second resolution.

12. The method of claim 7, wherein processing the infrared image to identify a thermal image object within the scene comprises adjusting a quantization level of the infrared image.

13. The method of claim 7, wherein processing the infrared image to identify a thermal image object within the scene comprises adjusting a threshold level of the infrared image.

14. The method of claim 7, further comprising matching the scaled second object area to the thermal object area.

* * * * *